United States Patent
Maruo Oliveira

(10) Patent No.: US 12,262,829 B2
(45) Date of Patent: Apr. 1, 2025

(54) DONNING AND DOFFING AID FOR A SUPPORT STOCKING

(71) Applicant: SIGVARIS AG, St. Gallen (CH)

(72) Inventor: Yuki Melany Maruo Oliveira, Winterthur (CH)

(73) Assignee: SIGVARIS AG, St. Gallen (CH)

( * ) Notice: Subject to any disclaimer, the term of this patent is extended or adjusted under 35 U.S.C. 154(b) by 0 days.

(21) Appl. No.: 18/026,695

(22) PCT Filed: Aug. 6, 2021

(86) PCT No.: PCT/EP2021/072057
§ 371 (c)(1),
(2) Date: Mar. 16, 2023

(87) PCT Pub. No.: WO2022/078650
PCT Pub. Date: Apr. 21, 2022

(65) Prior Publication Data
US 2023/0346148 A1 Nov. 2, 2023

(30) Foreign Application Priority Data
Oct. 14, 2020 (CH) ........................................ 1305/20

(51) Int. Cl.
*A47G 25/90* (2006.01)

(52) U.S. Cl.
CPC .................................. *A47G 25/905* (2013.01)

(58) Field of Classification Search
CPC .... A47G 25/90; A47G 25/905; A47G 25/907; A47G 25/908
See application file for complete search history.

(56) References Cited

U.S. PATENT DOCUMENTS

| | | | | |
|---|---|---|---|---|
| 2,894,669 A | * | 7/1959 | Silken | A47G 25/905 223/111 |
| 4,943,097 A | * | 7/1990 | Sanger | A47G 25/908 223/111 |
| 5,636,650 A | * | 6/1997 | Kroeze | A45B 9/00 135/70 |
| 5,924,610 A | * | 7/1999 | Willemin | A47G 25/905 223/111 |

(Continued)

FOREIGN PATENT DOCUMENTS

| | | |
|---|---|---|
| CH | 692472 A5 | 7/2002 |
| DE | 102011013217 A1 | 3/2012 |

(Continued)

OTHER PUBLICATIONS

Sigvaris AG; International Application No. PCT/EP2021/072057 filed Aug. 6, 2021; International Search Report and Written Opinion; ISA/EP; Dec. 13, 2021; 9 pp.

*Primary Examiner* — Ismael Izaguirre
(74) *Attorney, Agent, or Firm* — FisherBroyles LLP; Anthony J DoVale

(57) ABSTRACT

A donning and doffing aid is used for donning and doffing a stocking, in particular a compression stocking. The donning and doffing aid comprises a support element (1) which is adapted in such a way that the stocking can be spanned on it in a tubular manner. Furthermore, the donning and doffing aid has at least one protrusion (4) on which the stocking (6) can be spanned for doffing.

16 Claims, 2 Drawing Sheets

(56) References Cited

U.S. PATENT DOCUMENTS

| | | | |
|---|---|---|---|
| 6,942,129 B2 * | 9/2005 | Ferraioli | A47G 25/908 |
| | | | 223/118 |
| 7,070,074 B2 | 7/2006 | Landsberger et al. | |
| 8,215,524 B1 * | 7/2012 | Swisher | A47G 25/908 |
| | | | 223/111 |
| 2005/0115994 A1 * | 6/2005 | Delamare | A47G 25/905 |
| | | | 223/112 |
| 2014/0263486 A1 | 9/2014 | Taylor | |

FOREIGN PATENT DOCUMENTS

| | | | | |
|---|---|---|---|---|
| EP | 3329808 B1 | 3/2019 | | |
| GB | 2221604 A | 2/1990 | | |
| GB | 2439400 A * | 12/2007 | | A47G 25/80 |
| IT | BA20090045 A1 | 4/2011 | | |

* cited by examiner

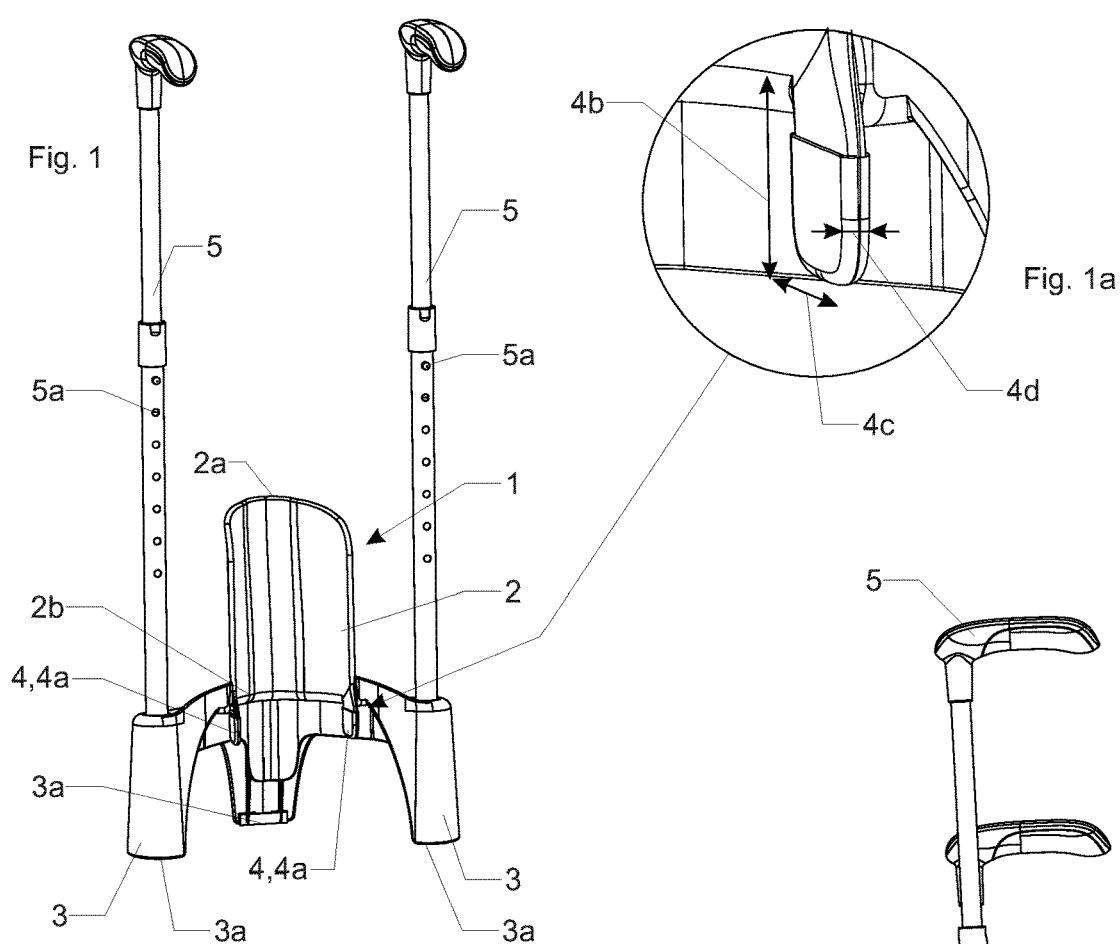
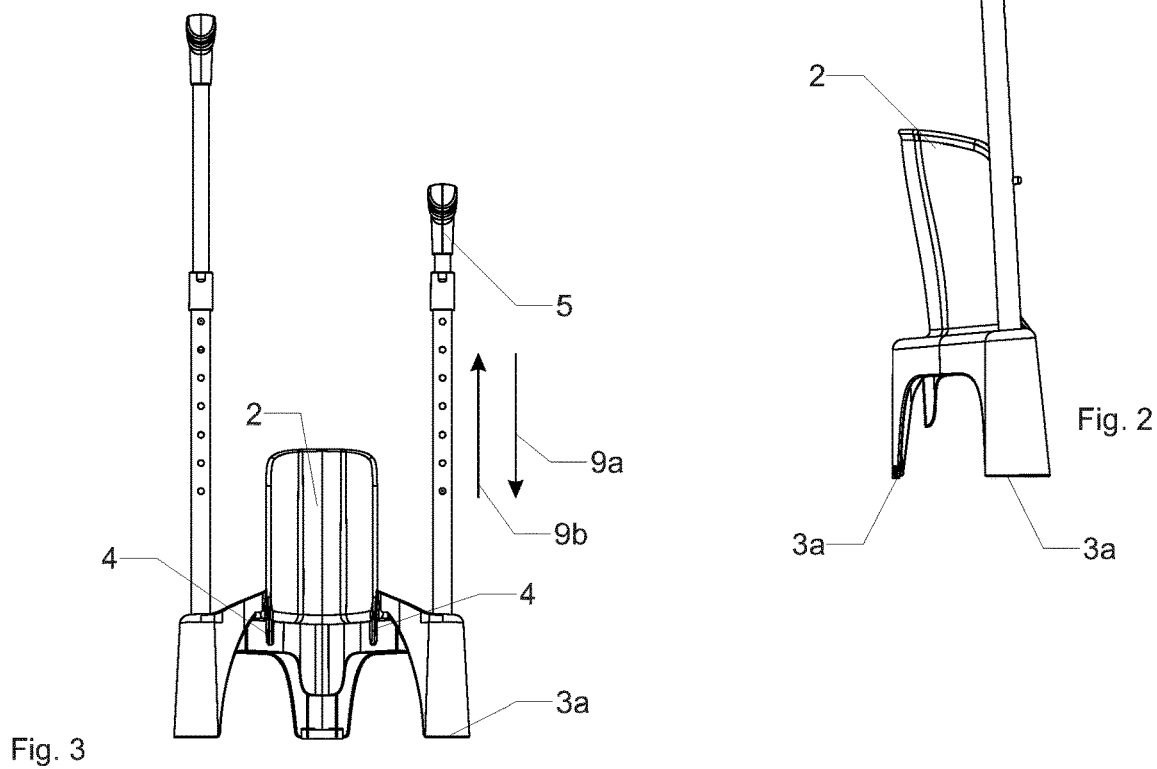

DONNING AND DOFFING AID FOR A SUPPORT STOCKING

TECHNICAL FIELD

The invention relates to a donning and doffing aid for donning and doffing a stocking, in particular a compression stocking. The donning and doffing aid comprises a support element which is adapted in such a way that the stocking can be spanned on it in a tubular manner. The invention also relates to a method for doffing a stocking with a donning and doffing aid.

BACKGROUND ART

Compression stockings are used, for example, for the prevention of thrombosis, the treatment of varicose veins, leg vein thrombosis, chronic venous insufficiency, post-thrombotic syndrome, lymphoedema or lipoedema. They create external pressure on the tissue of the enclosed leg to relieve its damaged venous or lymphatic system. Compression stockings are also used in sports and leisure.

Donning and doffing of compression stockings can be particularly difficult for people with limited mobility, for older or elderly people. Such persons are either dependent on external assistance or can easily don and/or doff the compression stocking with a donning and/or doffing aid.

DISCLOSURE OF THE INVENTION

The object of the present invention is to provide a donning and doffing aid which is compact and easy to use.

This object is solved by the subject of the independent claim. Accordingly, a donning and doffing aid for donning and doffing a stocking, in particular a compression stocking, comprises a support element. This is adapted in such a way that the stocking can be spanned on it in a tubular manner, in particular for doffing.

Tubular means that the stocking forms a hollow shape into which the body part to be treated, in particular the leg, can be easily inserted. The stocking is thus not folded flat, but includes an opening for the insertion of the body part to be treated. This makes the stocking particularly easy to don. In particular, the tube shape has a semi-circular cross-section.

The donning and doffing aid comprises at least one protrusion on which the stocking can be spanned for doffing. The at least one protrusion may also be referred to as a doff tab. The donning and doffing aid can thus support both donning and doffing. The design of the doffing aid in the form of at least one protrusion is geometrically very simple and thus easy to use.

Advantageously, the support element has a trough-shaped or partially tubular guide with a first end and a second end. Partially tubular means that a body part is not completely enclosed by the guide, but only partially. In other words, the tubular profile is not completely surrounding, but for example only semi-circular.

In particular, the guide is configured such that it can at least partially enclose the body part to be treated, in particular a leg. Preferably, the stocking can be spanned on the guide.

On the one hand, a trough-shaped or partially tubular guide allows reliable and comfortable guidance of the body part to be treated. On the other hand, its open design allows body parts of different sizes to be treated to be guided through the guide. Furthermore, the guide does not need to be a completely surrounding tube, since the partially tubular spanning of the stocking is sufficient to insert the body part to be treated into the stocking.

In particular, in intended use, the first end is directed upwards, i.e. towards the body, and the second end is directed downwards, i.e. away from the body. For example, if the stocking is donned while seated, the second end is directed towards the ground and the first end is directed towards the body.

In particular, the stocking can be spanned at the first end of the guide for donning and/or at the second end of the guide for doffing. For the latter, the at least one protrusion is provided at the second end.

Furthermore, the at least one protrusion can be directed downwards, i.e. away from the body, in the intended use. The orientation towards the bottom has in particular the advantage that during doffing the protrusions are directed in the direction of doffing and therefore the stocking is reliably fixed to the donning and doffing aid.

In particular, the at least one protrusion extends away from the support element in a first direction, while at least one handle, in particular exactly two handles, extends away from the support element in a direction opposite to the first direction.

Preferably, the first and/or the second end of the guide are designed to be open, i.e. the body part to be treated can be inserted into the guide without effort.

In particular, the at least one protrusion is arranged at the second end of the guide, and in particular is adapted such that the protrusion extends in the direction of the guide, and in particular away from the guide.

The direction of the guide is the direction in which the body part to be treated is intended to be moved by the guide. In other words, the protrusion lies in the extension of the guide.

Advantageously, the donning and doffing aid has two protrusions which are arranged diametrically opposite each other on a semi-circular guide. Diametrically means opposite in diameter. Thus, if the guide is semi-circular, the two protrusions are arranged at the two end points of the semi-circle. Such an arrangement of the protrusions allows the stocking to be easily spanned in order to doff.

In particular, the at least one protrusion comprises a cap, in particular made of an elastomer. This cap allows the stocking to be received gently so that the stocking is not damaged when force is applied to it. It also improves the adhesion between the stocking and the doffing aid.

Preferably, at least one handle, in particular exactly two handles, is arranged on the support element, which handle is in particular extendable, and/or can be extended to a length of at least 40 cm, in particular at least 50 cm, and/or has a latching device, in particular a snap head, for fixing its length. A long handle has the advantage that the stocking can be pulled over the legs in a sitting position without difficulty and the donning and doffing aid can be held in place with the hands.

In particular, the at least one protrusion is arranged between the two handles. This allows easy, and stable holding of the donning and doffing device with both hands during donning and doffing of a stocking. The user comfort is thereby increased.

In particular, the at least one protrusion
has an extension of at least 10 mm, in particular of at least 20 mm, and/or of at most 60 mm, in particular of at most 40 mm, in particular of at most 30 mm, and/or
a thickness of at most 20 mm, in particular of at most 10 mm, and/or a width of at most 60 mm, in particular of at most 50 mm, in particular of at most 40 mm.

Advantageously, the donning and doffing aid comprises support devices. These are adapted in such a way that the undersides of the support devices can support the donning and doffing aid against a plane while a stocking put on the body is spanned onto the donning and doffing aid. If the donning and doffing aid can be supported on the ground, the user has both hands free to span the stocking onto the donning and doffing aid.

Further protected is a method of doffing a stocking using a donning and doffing aid as described. The method comprises the following steps:

Spanning, in particular by hand, the stocking from below over the at least one protrusion;

moving the donning and doffing aid downwards or pulling up the leg while the opening of the stocking is pulled downwards by the donning and doffing aid.

This method allows the stocking to be doffed as easily as possible, even for persons who are restricted in their mobility.

In particular, the donned stocking is pulled downwards to the middle of the calf before it is spanned.

Advantageously, the donning and doffing aid is supported on a floor during donning.

In addition, the method may comprise the following steps for donning the stocking:

spanning the opening of the stocking on a first end of the guide;

grasping handles;

inserting the foot into the stocking and simultaneously supporting the donning and doffing aid with the undersides of the support device on a floor.

BRIEF DESCRIPTION OF THE DRAWINGS

Further embodiments, advantages and applications of the invention will be apparent from the dependent claims and from the description which now follows with reference to the figures.

FIG. 1 shows a first view of a donning and doffing aid;
FIG. 1a shows a detailed view of FIG. 1;
FIG. 2 shows a side view of the donning and doffing aid;
FIG. 3 shows a front view of the donning and doffing aid.

MODE FOR CARRYING OUT THE INVENTION

Figure 4A:
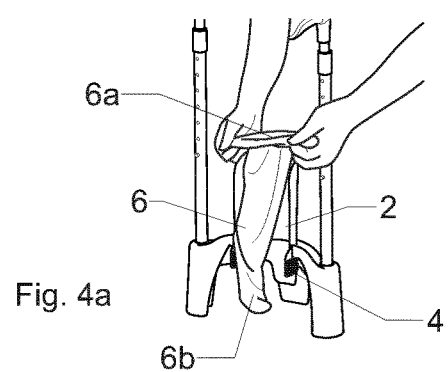
FIGS. 4a to 4d shows the donning of a stocking; and ing.

FIGS. 1 to 3 show a donning and doffing aid according to the invention. This comprises a support element 1 which is arranged centrally. The support element 1 comprises a guide 2 and support devices 3.

The guide 2 is partially tubular. I.e. it forms a half tube, which has a profile of a semicircle. The guide 2 extends from a first end 2a to a second end 2b. The first end 2a is directed upwards when used as intended and the second end 2b is directed downwards when used as intended. The first end 2a and the second end 2b are open, i.e. there are no walls that would close the ends of the guide 2. The guide 2 is also trough-shaped. The support devices 3 are arranged in such a way that their lower sides 3a can support the donning and doffing aid against a plane below.

A stocking can be spanned on the first side 2a of the guide for donning. The donning process is described in more detail in FIGS. 4a to 4d. When a leg is inserted into the stretched stocking, the guide 2 encloses half of the leg from behind.

Two protrusions 4 are arranged at the second end 2b of the guide 2. These have rubber caps 4a. The donned stocking can be fixed to these protrusions 4 in order to doff it from the leg by means of the donning and doffing aid. As shown in FIG. 1a, the protrusions comprise an extension 4b of about 25 to 40 mm, a width 4c of about 32 mm and a thickness 4d of about 6 mm.

Handles 5 are also arranged on the support element 1. These handles 5 are extendable and have latching devices 5a, in this case snap heads, to fix the length of the handles 5. The handles 5 can be removed from the support element 1.

Figure 4B:
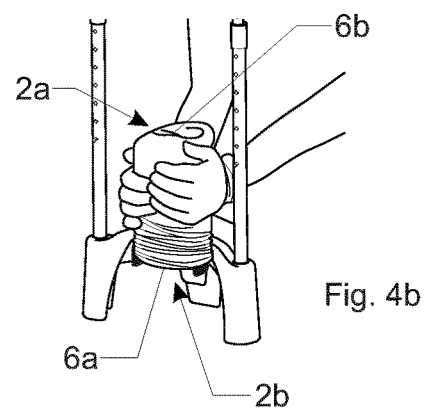

FIGS. 4a to 4d show a stocking 6 being donned. The opening 6a of the stocking 6 is spanned onto the first end 2a of the guide 2. Subsequently, the stocking 6 is further fitted over the guide 2 until the foot part 6b of the stocking 6 arrives at the first, upper end 2a of the guide 2 and the opening 6a of the stocking is located at the lower, second end 2b of the guide 2. The fully spanned stocking 6 is shown in FIG. 4b.

Figure 4C:
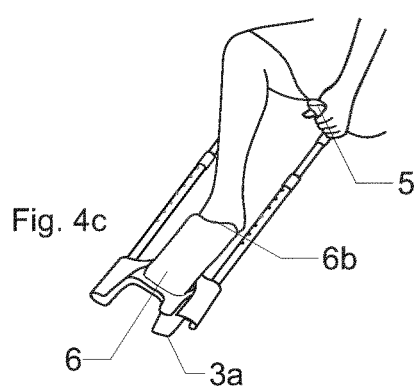

The user grips the handles 5 with his hands while sitting or standing. This is shown in FIG. 4c. He brings his foot to the first, upper end 2a of the guide 2 and comes into contact with the foot part 6b of the stocking 6. At the same time, the user supports the donning and doffing aid on the floor with the lower sides 3a of the support device 3.

Figure 4D:
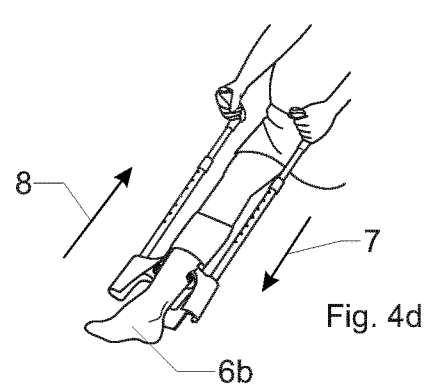

As shown in FIG. 4d, the user then moves his leg further down along the guide 3 and moves the foot part 6b of the stocking 6 into the opened stocking 6. The direction of movement is also illustrated with the arrow 7 and represents the direction of the guide 3. The user continues to move his foot until it reaches the ground or he is able to extend his leg. In order to pull the stocking 6 up completely, the user pulls the donning and doffing aid towards him, i.e. in the direction of the arrow 8. The stocking is then completely put on and the donning and doffing aid can be removed.

Figure 5A:
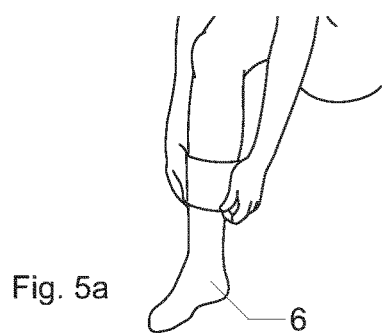
FIGS. 5a to 5d shows the doffing of a stocking.
Figure 5B:
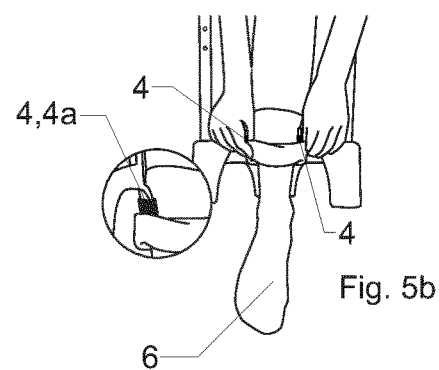

FIGS. 5a to 5d show the doffing of the stocking 6. In a first step, the user pulls the stocking 6 down to the middle of the calf, as shown in FIG. 5a. Then the stocking 6 is put over the two protrusions 4 from below. The protrusions 4 are marked in black. In addition, the protrusions 4 have rubber caps 4a which protect the stocking 6.

Figure 5C:
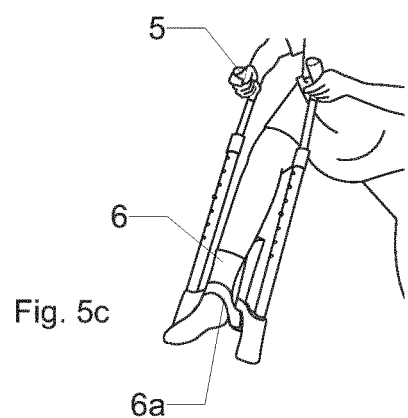
Figure 5D:
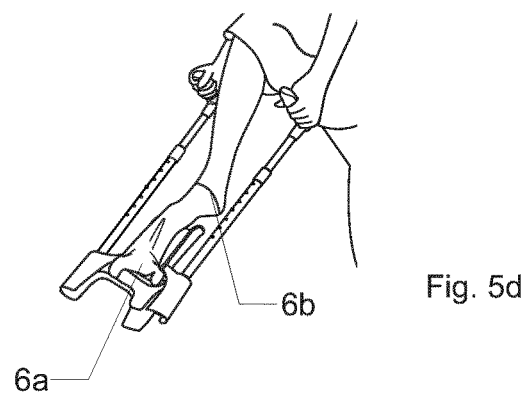

Subsequently, as shown in FIG. 5c, the user moves the donning and doffing aid downwards or pulls up his leg while the opening 6a of the stocking 6 is pulled downwards. This movement continues until the foot is completely removed from the stocking 6, as shown in FIG. 5d.

The orientation of the protrusions 4 downwards or away from the body has the advantage that the opening 6a of the stocking 6 reliably adheres to the protrusions 4 as it is moved downwards and remains adhered there while the user pulls his leg out of the stocking 6.

The protrusions 4 thus extend in a first direction 9a (shown in FIG. 3) away from the support element, while the handles 5 extend in a direction 9b opposite to the first direction.

While preferred embodiments of the invention are described in the present application, it should be clearly noted that the invention is not limited thereto and may also be carried out in other ways within the scope of the following claims.

The invention claimed is:

1. A donning and doffing aid for donning and doffing a stocking, in particular a compression stocking, comprising:
   a support element;
   wherein the stocking can be spanned on the support element in a tubular manner for donning, at least one protrusion on which the stocking can be spanned for doffing, wherein the support element has a guide with a first end and a second end, wherein the guide is adapted to at least partially enclose a body part, wherein the first end of the guide is open, the second end of the guide is open, or the first end and the second end of the guide are open, and wherein the donning and doffing aid comprises two protrusions, the guide has a semi-circular profile, and the two protrusions are arranged diametrically opposite each other at the second end of the guide with the semi-circular profile.

2. The donning and doffing aid according to claim 1, wherein, during seated donning and doffing, the first end of the guide is directed upwards and the second end of the guide is directed downwards.

3. The donning and doffing aid according to claim 1, wherein the at least one protrusion is arranged at the second end of the guide, and extends in the direction of the guide.

4. The donning and doffing aid according to claim 1, wherein the at least one protrusion is directed downwards during seated donning and doffing.

5. The donning and doffing aid according to claim 1, wherein the at least one protrusion comprises a cap made of an elastomer.

6. The donning and doffing aid according to claim 1 wherein at least one handle is arranged on the support element, which is extendable, is extendable to a length of at least 40 cm, is extendable to at least 50 cm, or has a latching device for fixing a length of the at least one handle.

7. The donning and doffing aid according to claim 6, wherein the at least one protrusion extends away from the support element in a first direction and the at least one handle extends away from the support element in a direction opposite to the first direction.

8. The donning and doffing aid according to claim 6, comprising two handles.

9. The donning and doffing aid of claim 8 wherein the at least one protrusion is arranged between the two handles.

10. The donning and doffing aid of claim 6 wherein the latching device is a snap head.

11. The donning and doffing aid according to claim 1, wherein the at least one protrusion has an extension of at least 10 mm, at least 20 mm, and of at most 60 mm, at most 40 mm, or at most 30 mm;

wherein the at least one protrusion has a thickness of at most 20 mm or at most 10 mm;

wherein the at least one protrusion has a width of at most 60 mm, at most 50 mm, or at most 40 mm.

12. The donning and doffing aid according to claim 1 further comprising support devices with undersides of the support devices adapted to support the donning and doffing aid on a plane while a donned stocking is spanned onto the donning and doffing aid.

13. A method of doffing a stocking by means of a donning and doffing aid according to claim 1, wherein the method of doffing comprises the following steps:

spanning, in particular by hand, the stocking from below, over the at least one protrusion;

moving the donning and doffing aid downwards or pulling up a leg while the opening of the stocking is being pulled downwards by the donning and doffing aid.

14. The method according to claim 13, wherein during the spanning, the donning and doffing aid is supported on a floor.

15. The method according to claim 13 further including method steps for donning the stocking comprising:

spanning the opening of the stocking on the first end of the guide;

grasping handles;

inserting a foot into the stocking and simultaneously supporting the donning and doffing aid with the lower sides of the support device on a floor.

16. The donning and doffing aid of claim 1 wherein the guide is trough-shaped, partially tubular, or semi-tubular.

* * * * *